United States Patent
Totsuka et al.

(10) Patent No.: US 10,638,998 B2
(45) Date of Patent: May 5, 2020

(54) X-RAY DIAGNOSTIC APPARATUS AND MEDICAL-INFORMATION PROCESSING APPARATUS CONFIGURED TO CONTROL A ROTATING SPEED OF A ROTARY ANODE OF AN X-RAY TUBE BY DERIVING AN ACQUIRING CONDITION FROM A FLUOROSCOPIC IMAGE

(71) Applicant: Toshiba Medical Systems Corporation, Otawara-shi (JP)

(72) Inventors: Yuki Totsuka, Nasushiobara (JP); Masaharu Soya, Nasushiobara (JP); Katsuo Takahashi, Yaita (JP); Kansei Takahashi, Nasushiobara (JP); Akira Mochiduki, Nasushiobara (JP); Katsunori Kojima, Hadano (JP); Daisuke Sato, Utsunomiya (JP); Hisayuki Uehara, Otawara (JP); Hiroyoshi Kobayashi, Nasushiobara (JP); Akio Tetsuka, Shioyagun (JP)

(73) Assignee: Canon Medical Systems Corporation, Otawara-shi (JP)

( * ) Notice: Subject to any disclaimer, the term of this patent is extended or adjusted under 35 U.S.C. 154(b) by 292 days.

(21) Appl. No.: 15/616,342

(22) Filed: Jun. 7, 2017

(65) Prior Publication Data
US 2017/0352518 A1    Dec. 7, 2017

(30) Foreign Application Priority Data
Jun. 7, 2016 (JP) ................. 2016-113210

(51) Int. Cl.
*A61B 6/00* (2006.01)
*H05G 1/26* (2006.01)
(Continued)

(52) U.S. Cl.
CPC ............. *A61B 6/545* (2013.01); *A61B 6/06* (2013.01); *A61B 6/40* (2013.01); *A61B 6/465* (2013.01);
(Continued)

(58) Field of Classification Search
CPC .......... A61B 6/06; A61B 6/486; A61B 6/487; A61B 6/54; A61B 6/542; A61B 6/545;
(Continued)

(56) References Cited

U.S. PATENT DOCUMENTS

| 5,809,106 A * | 9/1998 | Kitade ................. H01J 35/101 378/117 |
| 5,883,487 A * | 3/1999 | Rosenzweig ............. G01P 3/48 318/459 |

(Continued)

FOREIGN PATENT DOCUMENTS

| JP | 2000-286092 | 10/2000 |
| JP | 2001-76895 | 3/2001 |

(Continued)

*Primary Examiner* — Allen C. Ho
(74) *Attorney, Agent, or Firm* — Oblon, McClelland, Maier & Neustadt, L.L.P.

(57) ABSTRACT

An X-ray diagnostic apparatus comprises an X-ray tube and processing circuitry. The X-ray tube includes a rotary anode. The processing circuitry is configured to derive an acquiring condition from a fluoroscopic image, and start to increase, in accordance with the acquiring condition derived, a rotating speed of the anode from a low rotating speed to a high rotating speed before the X-ray tube finishes emitting an X-ray to acquire the fluoroscopic image.

18 Claims, 9 Drawing Sheets

(51) Int. Cl.
*H05G 1/30* (2006.01)
*H05G 1/66* (2006.01)
*H01J 35/10* (2006.01)
*H01J 35/26* (2006.01)
*A61B 6/06* (2006.01)

(52) U.S. Cl.
CPC ............... *A61B 6/48* (2013.01); *A61B 6/486* (2013.01); *A61B 6/487* (2013.01); *A61B 6/54* (2013.01); *A61B 6/542* (2013.01); *H01J 35/10* (2013.01); *H01J 35/101* (2013.01); *H01J 35/26* (2013.01); *H05G 1/26* (2013.01); *H05G 1/265* (2013.01); *H05G 1/30* (2013.01); *H05G 1/66* (2013.01); *A61B 6/4441* (2013.01)

(58) Field of Classification Search
CPC ............ H05G 1/26; H05G 1/265; H05G 1/30; H05G 1/34; H05G 1/66; H01J 35/10; H01J 35/101; H01J 35/26
USPC ........... 378/42, 62, 98.7, 125, 131, 132, 144
See application file for complete search history.

(56) References Cited

U.S. PATENT DOCUMENTS

| | | | | |
|---|---|---|---|---|
| 5,917,882 | A * | 6/1999 | Khutoryansky | A61B 6/08 378/108 |
| 6,480,569 | B2 * | 11/2002 | Sato | H01J 35/10 378/125 |
| 7,336,766 | B2 * | 2/2008 | Kitami | H05G 1/66 378/101 |
| 7,460,635 | B2 * | 12/2008 | Fujimoto | A61B 6/032 378/16 |
| 9,036,785 | B2 * | 5/2015 | Saito | H01J 35/26 378/101 |
| 9,900,971 | B2 * | 2/2018 | Shindo | H05G 1/66 |
| 10,111,639 | B2 * | 10/2018 | Karahashi | A61B 6/54 |

FOREIGN PATENT DOCUMENTS

| | | |
|---|---|---|
| JP | 2013-182764 | 9/2013 |
| JP | 2014-191935 | 10/2014 |
| WO | WO 2010/061809 A1 | 6/2010 |

* cited by examiner

X-RAY DIAGNOSTIC APPARATUS AND MEDICAL-INFORMATION PROCESSING APPARATUS CONFIGURED TO CONTROL A ROTATING SPEED OF A ROTARY ANODE OF AN X-RAY TUBE BY DERIVING AN ACQUIRING CONDITION FROM A FLUOROSCOPIC IMAGE

CROSS-REFERENCE TO RELATED APPLICATIONS

This application is based upon and claims the benefit of priority from Japanese Patent Application No. 2016-113210, filed on Jun. 7, 2016; the entire contents of which are incorporated herein by reference.

FIELD

Embodiments described herein relate generally to an X-ray diagnostic apparatus and a medical-information processing apparatus.

BACKGROUND

X-ray diagnostic apparatuses, including a rotary-anode type X-ray tube, sometimes have three rotation modes, i.e., a stopped state, a low rotating speed, and a high rotating speed. For example, in the case of the low rotating speed, the X-ray diagnostic apparatus may emit X-rays in a fluoroscopy mode and in an acquiring mode with a low radiation dose. In the case of the high rotating speed, the X-ray diagnostic apparatus may emit X-rays in a fluoroscopy mode, in an acquiring mode with a low radiation dose, and in an acquiring mode with a high radiation dose.

However, the X-ray diagnostic apparatus needs time to increase the rotating speed of the anode from the stopped state or the low rotating speed to the high rotating speed. Furthermore, if the X-ray tube emits X-rays in such a state that the rotating speed of the anode is insufficient, there is a possibility that the anode is melted due to the heat that is caused by electron collision. Therefore, conventional X-ray diagnostic apparatuses start to acquire fluoroscopic images and acquisition images with delay.

DETAILED DESCRIPTION

An X-ray diagnostic apparatus according to embodiments comprises an X-ray tube and processing circuitry. The X-ray tube includes a rotary anode. The processing circuitry is configured to derive an acquiring condition from a fluoroscopic image. And the processing circuitry is configured to start to increase, in accordance with the acquiring condition derived, a rotating speed of the anode from a low rotating speed to a high rotating speed before the X-ray tube finishes emitting an X-ray to acquire the fluoroscopic image.

With reference to the drawings, an explanation is given below of the X-ray diagnostic apparatus according to an embodiment. Furthermore, in the following embodiment, duplicated explanation is appropriately omitted.

Figure 1:
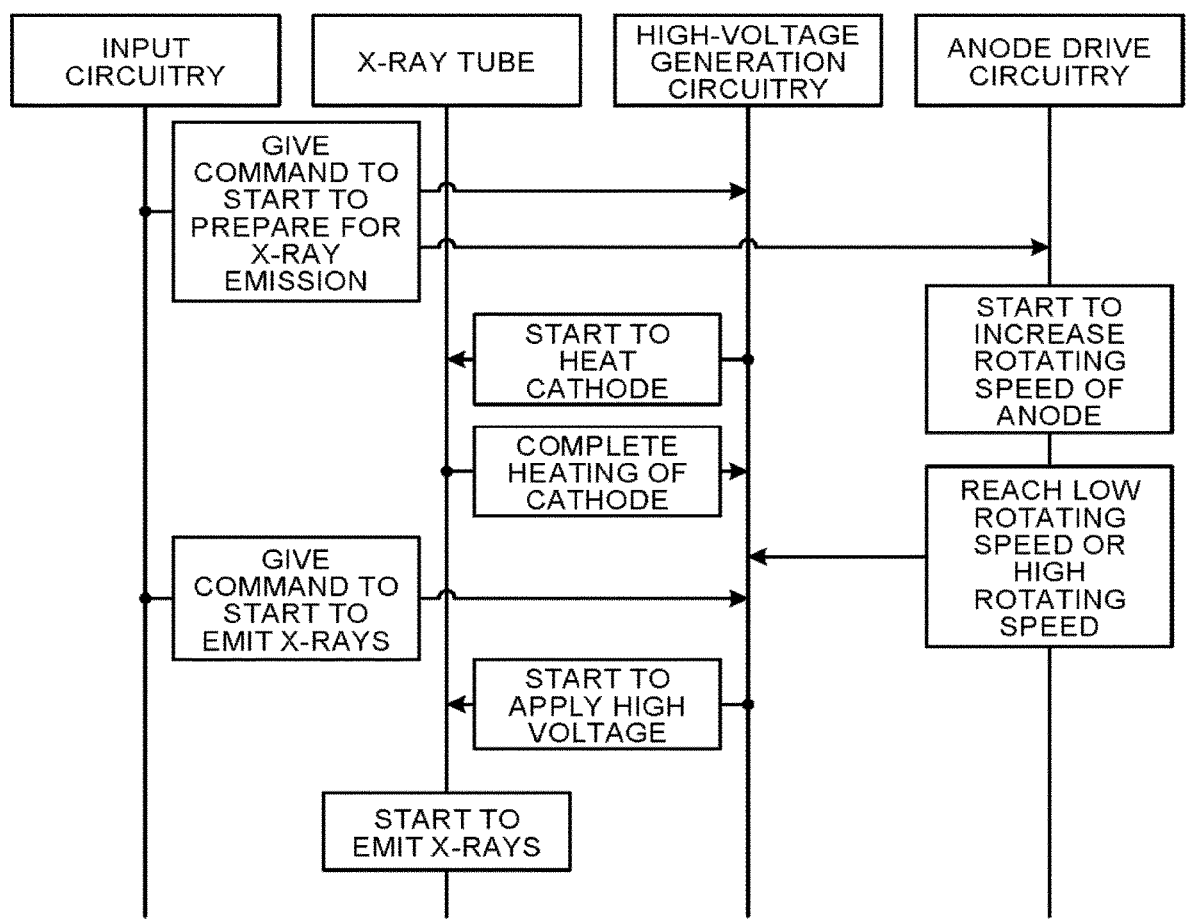
FIG. 1 is a sequence diagram that illustrates an example of the procedure before the conventional X-ray diagnostic apparatus starts to acquire a fluoroscopic image or acquire an acquisition image.
Figure 2:
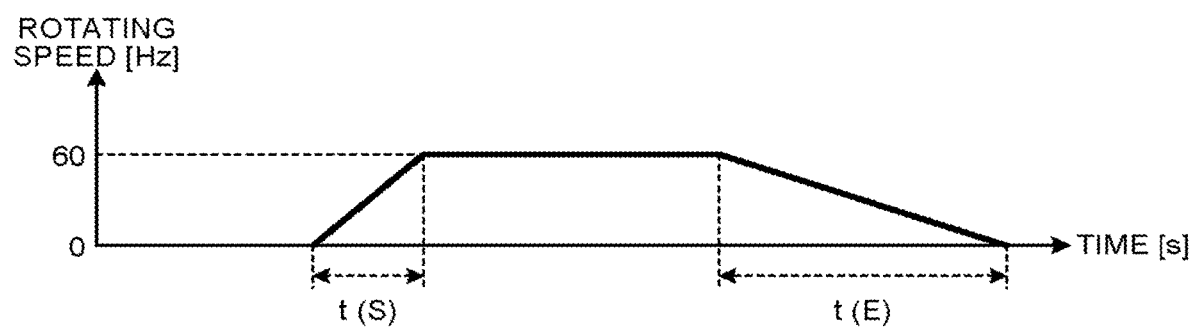
FIG. 2 is a diagram that illustrates an example of the case where the conventional X-ray diagnostic apparatus increases the rotating speed of the anode from the stopped state to the low rotating speed and decreases from the low rotating speed to the stopped state.
Figure 3:
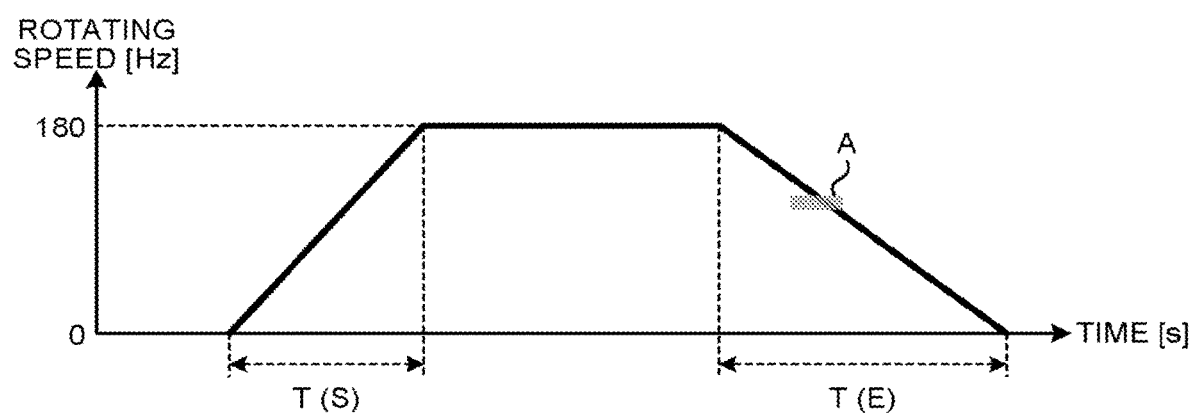
FIG. 3 is a diagram that illustrates an example of the case where the conventional X-ray diagnostic apparatus increases the rotating speed of the anode from the stopped state to the high rotating speed and decreases from the high rotating speed to the stopped state.

First, in order to make it easy to understand processes of the X-ray diagnostic apparatus according to the first embodiment, with reference to FIGS. 1, 2, and 3, an explanation is given of how a conventional X-ray diagnostic apparatus increases the rotating speed of the anode of the X-ray tube from the stopped state to the low rotating speed or the high rotating speed and decreases the rotating speed of the anode from the low rotating speed or the high rotating speed to the stopped state. FIG. 1 is a sequence diagram that illustrates an example of the procedure before the conventional X-ray diagnostic apparatus starts to acquire a fluoroscopic image or acquire an acquisition image. FIG. 2 is a diagram that illustrates an example of the case where the conventional X-ray diagnostic apparatus increases the rotating speed of the anode from the stopped state to the low rotating speed and decreases from the low rotating speed to the stopped state. FIG. 3 is a diagram that illustrates an example of the case where the conventional X-ray diagnostic apparatus increases the rotating speed of the anode from the stopped state to the high rotating speed and decreases from the high rotating speed to the stopped state.

As illustrated in FIG. 1, the conventional X-ray diagnostic apparatus includes input circuitry, the X-ray tube, high-voltage generation circuitry, and anode drive circuitry. For example, in accordance with a user's operation, the input circuitry transmits a command to the high-voltage generation circuitry and the anode drive circuitry so as to start to prepare for X-ray emission. In accordance with the command, the high-voltage generation circuitry starts to apply heat to the cathode of the X-ray tube. If heating of the cathode is completed, the X-ray tube transmits the message indicating it to the high-voltage generation circuitry. In accordance with the command, the anode drive circuitry starts to increase the rotating speed of the anode from the stopped state to the low rotating speed or the high rotating speed. If the rotating speed of the anode reaches the low rotating speed or the high rotating speed, the anode drive circuitry transmits the message indicating it to the high-voltage generation circuitry. For example, in accordance with a user's operation, the input circuitry transmits a command to the high-voltage generation circuitry so as to start to emit X-rays. In accordance with the command, the high-voltage generation circuitry applies a high voltage to the X-ray tube so as to start to emit X-rays.

When a fluoroscopic image of the subject is acquired, the conventional X-ray diagnostic apparatus sets the rotating speed of the anode of the X-ray tube to the low rotating speed. The low rotating speed is for example 60 Hz. Furthermore, when an acquisition image of the subject is acquired, the conventional X-ray diagnostic apparatus sets the rotating speed of the anode of the X-ray tube to the high rotating speed. The high rotating speed is for example 180 Hz. Moreover, the rotating speed of the anode in the stopped state is 0 Hz.

Here, fluoroscopic images are X-ray images that are acquired in chronological order when a detector detects X-rays that are emitted from the X-ray tube. For example, fluoroscopic images are used for deriving an acquiring condition, observing a subject in real time, or the like. Fluoroscopic images often do enough with low image quality as compared with acquisition images; therefore, they are usually acquired by using low-dose X-rays compared to X-rays that are used for acquiring acquisition images.

Furthermore, acquisition images are X-ray images that are acquired when a detector detects X-rays that are emitted from the X-ray tube, and for example they are used for diagnostic imaging. Specifically, a user, such as a doctor, views acquisition images to find areas of lesion of a subject or consider treatment planning for areas of lesion. Therefore, acquisition images are usually acquired with high image quality by using high-dose X-rays as compared to X-rays that are used for acquiring fluoroscopic images.

As illustrated in FIG. 2, the anode drive circuitry needs at least a time t(S) to increase the rotating speed of the anode from the stopped state to the low rotating speed. The time t(S) is for example about 1 second. Furthermore, as illustrated in FIG. 3, the anode drive circuitry needs at least a time T(S) to increase the rotating speed of the anode from the stopped state to the high rotating speed. The time T(S) is for example about 2 seconds. It is difficult for the conventional X-ray diagnostic apparatus to conduct acquiring of fluoroscopic images and acquiring of acquisition images during the time t(S) and the time T(S). Therefore, with the conventional X-ray diagnostic apparatus, the start of acquiring of fluoroscopic images and acquiring of acquisition images is delayed.

As illustrated in FIG. 2, to decrease the rotating speed of the anode from the low rotating speed to the stopped state, the anode drive circuitry applies a brake to the rotation of the anode during at least a time t(E). The time t(E) is for example about 3 seconds. Furthermore, as illustrated in FIG. 3, to decrease the rotating speed of the anode from the high rotating speed to the stopped state, the anode drive circuitry applies a brake to the rotation of the anode during at least a time T(E). The time T(E) is for example about 3 seconds.

Specifically, although it is only necessary to applies a brake to the anode in the case of the rotating speed of the anode at which the anode resonates, as indicated by an area A in FIG. 3, the anode drive circuitry applies a brake to the anode during the time t(E) or the time T(E) all the time. Therefore, the conventional X-ray diagnostic apparatus causes the coil, which applies a brake to the anode, and the anode drive circuitry to generate heat more than necessary, and there is an increase in the energy that is needed to applies a brake to the anode. Furthermore, even if an acquisition image of a subject is acquired and then immediately an acquisition image of the next subject is acquired, the conventional X-ray diagnostic apparatus uniformly decreases the rotating speed of the anode to the stopped state. Therefore, the conventional X-ray diagnostic apparatus spends unnecessary time in increasing the rotating speed of the anode to the low rotating speed or the high rotating speed again. Furthermore, it is difficult for the conventional X-ray diagnostic apparatus to acquire acquisition images while the anode drive circuitry applies a brake to the rotation of the anode. Furthermore, if the anode is continuously rotated at the low rotating speed or the high rotating speed on a constant basis, the shaft bearing, which supports the anode, is degraded and the operating life of the X-ray tube is reduced.

Figure 4:
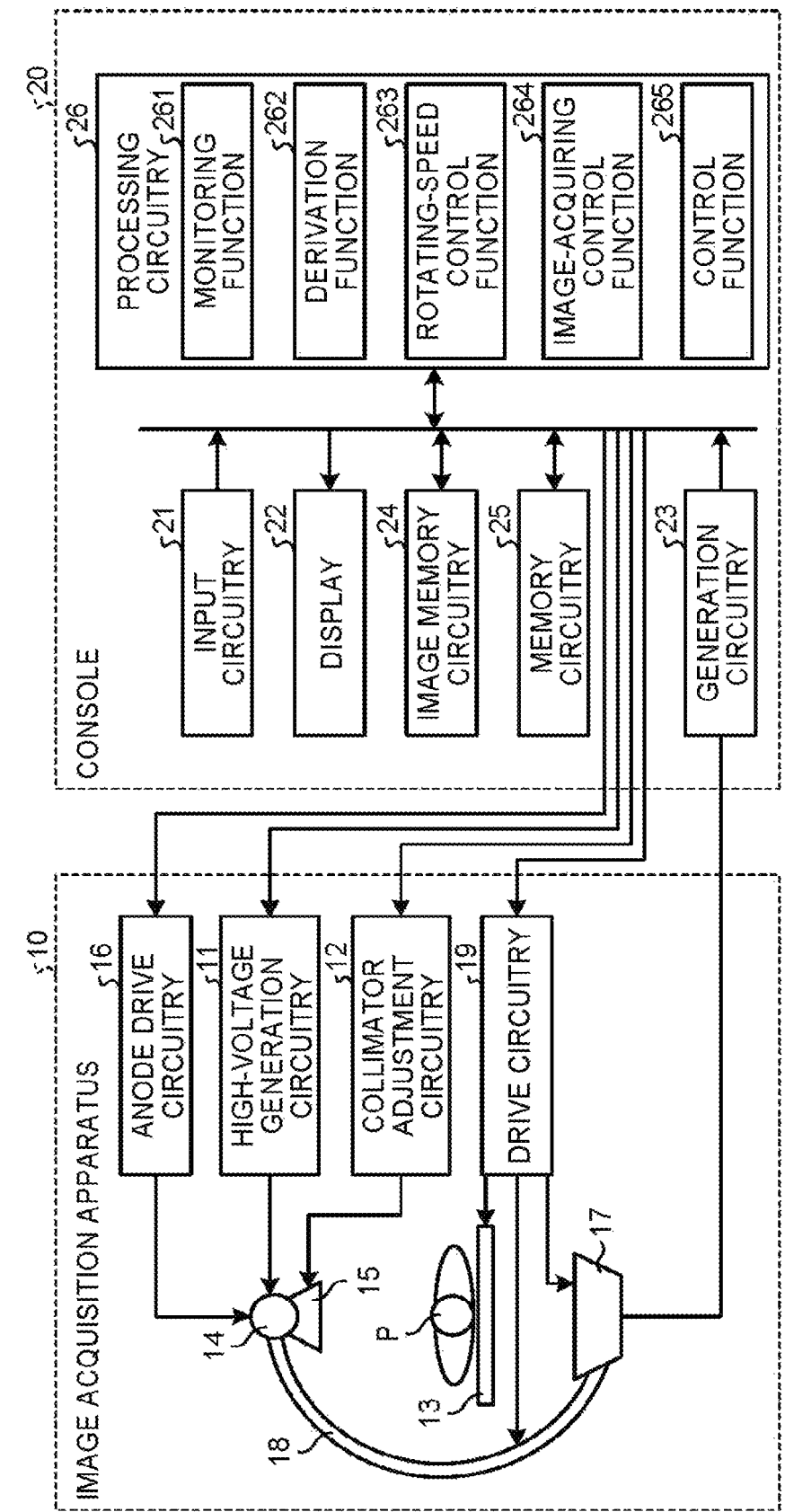
FIG. 4 is a block diagram that illustrates an example of the configuration of an X-ray diagnostic apparatus according to a first embodiment.

Next, with reference to FIG. 4, the configuration of an X-ray diagnostic apparatus 1 according to the first embodiment is explained. FIG. 4 is a block diagram that illustrates an example of the configuration of the X-ray diagnostic apparatus 1 according to the first embodiment. As illustrated in FIG. 4, the X-ray diagnostic apparatus 1 includes an image acquisition apparatus 10 and a console 20. Furthermore, the configuration of the X-ray diagnostic apparatus 1 is not limited to the configuration described below.

The image acquisition apparatus 10 includes high-voltage generation circuitry 11, collimator adjustment circuitry 12, a couch 13, an X-ray tube 14, a collimator 15, anode drive circuitry 16, an X-ray detector 17, a C arm 18, and drive circuitry 19.

The high-voltage generation circuitry 11 feeds a high voltage for the X-ray tube 14 to generate X-rays. The details of the high-voltage generation circuitry 11 are described later. The collimator adjustment circuitry 12 controls the collimator 15 to adjust the irradiation range of X-rays that are generated by the X-ray tube 14. The high-voltage generation circuitry 11 and the collimator adjustment circuitry 12 read and execute programs that are stored in memory circuitry 25, which is described later, to implement the functions.

The couch 13 is a bed that includes a tabletop, on which a subject P is placed. The X-ray tube 14 uses the high voltage, fed by the high-voltage generation circuitry 11, to generate X-rays that are emitted to the subject P. The details of the X-ray tube 14 are described later.

The collimator 15 adjusts the irradiation range of X-rays that are generated by the X-ray tube 14. The collimator 15 is provided between the X-ray tube 14 and the X-ray detector 17. The collimator 15 includes for example four slidable aperture blades. The collimator 15 slides the aperture blades to adjust the range within which the X-rays, generated by the X-ray tube 14, are emitted. In accordance with a command that is transmitted by a rotating-speed control function 263, which is described later, the anode drive circuitry 16 controls the rotating speed of an anode 142, which is described later, and applies a brake to the rotation of the anode 142. The anode drive circuitry 16 controls the current that flows through the coil, which generates the rotating magnetic field, to control the rotating speed of the anode 142 and apply a brake to the rotation of the anode 142.

The X-ray detector 17 detects X-rays that are emitted by the X-ray tube 14. The X-ray detector 17 is for example a Flat Panel Detector (FPD). The X-ray detector 17 includes detecting elements that are arranged in a matrix. The detecting element converts X-rays, emitted by the X-ray tube 14, into electric signals and stores them. The stored electric signals are transmitted to generation circuitry 23 that is described later.

The X-ray tube 14 and the collimator 15 are opposed to the X-ray detector 17 with the subject P interposed therebetween, and they are held by the C arm 18.

The drive circuitry 19 moves the C arm 18. The drive circuitry 19 changes the Source Image receptor Distance (SID), which is the distance between the X-ray tube 14 and the X-ray detector 17. Furthermore, the drive circuitry 19 is capable of rotating the X-ray detector 17, held by the C arm 18, within the plane in which the detecting elements are arranged in a matrix. Moreover, the drive circuitry 19 moves the tabletop, on which the subject P is placed, in a horizontal direction and in a vertical direction. The drive circuitry 19 reads and executes programs that are stored in the memory circuitry 25, which is described later, and implements the functions.

The console 20 includes input circuitry 21, a display 22, the generation circuitry 23, image memory circuitry 24, the memory circuitry 25, and processing circuitry 26.

The input circuitry 21 is used by a user who inputs commands or settings. The input circuitry 21 is included in for example a mouse or a keyboard. The input circuitry 21 transfers commands or settings, input by the user, to the processing circuitry 26. The input circuitry 21 is implemented by for example a processor.

The display 22 is a monitor that is viewed by the user. The display 22 is for example a liquid crystal display. For example, the display 22 receives commands to display fluoroscopic images, acquisition images, or the Graphical User Interface (GUI) from the processing circuitry 26. This allows the display 22 to present fluoroscopic images, acquisition images, and the GUI. The GUI is used when the user inputs commands or settings.

The generation circuitry 23 generates fluoroscopic images or acquisition images on the basis of electric signals that are output by each of the detecting elements. The generation circuitry 23 reads and executes programs that are stored in the memory circuitry 25, which is described later, to implement the functions. Here, the generation circuitry 23 is implemented by for example a processor.

The image memory circuitry 24 stores fluoroscopic images or acquisition images that are generated by the generation circuitry 23. The memory circuitry 25 stores programs for the high-voltage generation circuitry 11, the collimator adjustment circuitry 12, and the drive circuitry 19 to implement the above-described functions. The memory circuitry 25 stores programs for the generation circuitry 23 and the processing circuitry 26 to implement each function that is described later. The image memory circuitry 24 and the memory circuitry 25 include a storage medium, from which the stored information may be read by a computer. The storage medium is for example a hard disk.

The processing circuitry 26 includes a monitoring function 261, a derivation function 262, the rotating-speed control function 263, an image-acquiring control function 264, and a control function 265. The processing circuitry 26 is implemented by for example a processor.

The monitoring function 261 monitors the rotating speed of the anode 142 of the X-ray tube 14. The derivation function 262 derives an acquiring condition from a fluoroscopic image. In accordance with the derived acquiring condition, the rotating-speed control function 263 starts to increase the rotating speed of the anode 142 from the low rotating speed to the high rotating speed before the X-ray tube 14 finishes emitting X-rays to acquire fluoroscopic images. The low rotating speed is a rotating speed of the anode 142 to acquire fluoroscopic images. The high rotating speed is a rotating speed of the anode 142 to acquire fluoroscopic images or acquisition images. That is, the high rotating speed is a rotating speed higher than the low rotating speed. The details of the monitoring function 261, the derivation function 262, and the rotating-speed control function 263 are described later.

The image-acquiring control function 264 is a function to acquire fluoroscopic images or acquisition images by controlling the high-voltage generation circuitry 11, the collimator adjustment circuitry 12, the anode drive circuitry 16, the drive circuitry 19, and the generation circuitry 23. Specifically, the image-acquiring control function 264 performs the following control. First, the image-acquiring control function 264 controls the drive circuitry 19 to move the X-ray tube 14, the collimator 15, and the X-ray detector 17 to positions that are suitable for acquiring fluoroscopic images or acquisition images. Next, the image-acquiring control function 264 controls the high-voltage generation circuitry 11, the collimator adjustment circuitry 12, and the anode drive circuitry 16 so as to emit X-rays to the subject P. Then, the image-acquiring control function 264 controls the generation circuitry 23 so as to generate fluoroscopic images or acquisition images. Furthermore, if a moving image is acquired, the image-acquiring control function 264 controls the generation circuitry 23 so as to perform the above-described process on each frame of the moving image.

The image-acquiring control function 264 starts image acquiring in the interval from when the rotating speed of the anode 142 reaches the high rotating speed to when an elapsed time elapses. The elapsed time is time required to increase the low rotating speed to the high rotating speed after the X-ray tube 14 finishes emitting X-rays to acquire the fluoroscopic image. The details of the image-acquiring control function 264 are described later.

The control function 265 has the function to operate each component of the image acquisition apparatus 10 and the console 20 in accordance with a purpose at appropriate timing as well as other functions.

Figure 5:
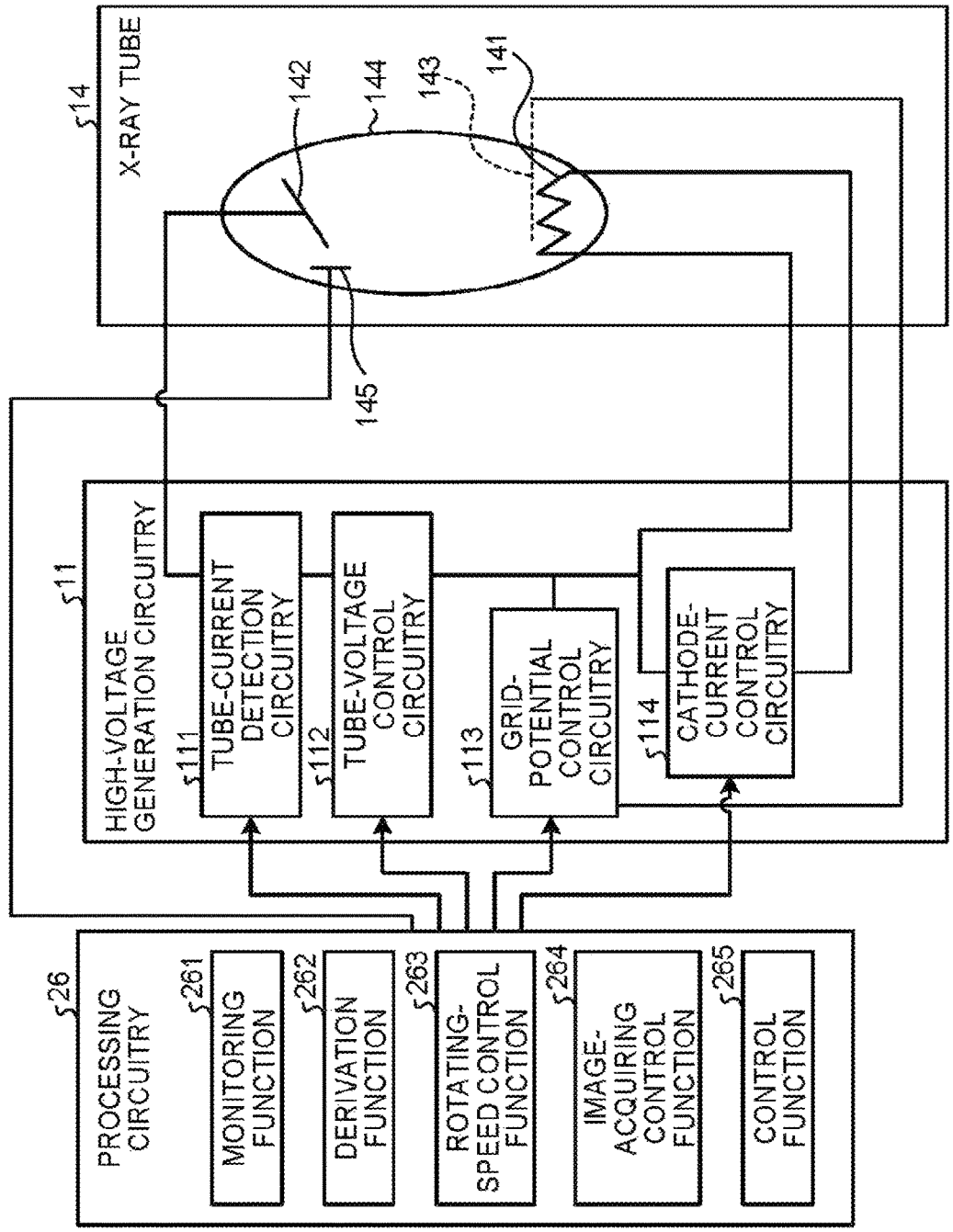
FIG. 5 is a diagram that illustrates an example of high-voltage generation circuitry, an X-ray tube, and processing circuitry according to the first embodiment.

Next, with reference to FIG. 5, an explanation is given of the high-voltage generation circuitry 11, the X-ray tube 14, and the processing circuitry 26, included in the X-ray diagnostic apparatus 1. FIG. 5 is a diagram that illustrates an example of the high-voltage generation circuitry 11, the X-ray tube 14, and the processing circuitry 26 according to the first embodiment.

As illustrated in FIG. 5, the X-ray diagnostic apparatus 1 includes the high-voltage generation circuitry 11, the X-ray tube 14, and the processing circuitry 26.

The high-voltage generation circuitry 11 includes tube-current detection circuitry 111, tube-voltage control circuitry 112, grid-potential control circuitry 113, and cathode-current control circuitry 114.

The tube-current detection circuitry 111 detects the tube current that flows between a cathode 141, which is described later, and the anode 142. Specifically, it acquires the time-series data on the tube current that flows between the cathode 141 and the anode 142. The tube-voltage control circuitry 112 controls the tube voltage that is applied between the cathode 141 and the anode 142. The grid-potential control circuitry 113 controls the electric potential of a grid 143 that is described later. The cathode-current control circuitry 114 controls the current that flows through the cathode 141 that is described later. Here, the tube-current detection circuitry 111, the tube-voltage control circuitry 112, the grid-potential control circuitry 113, and the cathode-current control circuitry 114 are implemented by for example a processor.

The X-ray tube 14 includes the cathode 141, the anode 142, the grid 143, a glass bulb 144, and a rotating-speed monitoring device 145.

The cathode 141 emits electrons. Specifically, the cathode 141 is heated due to the currents that are supplied by the cathode-current control circuitry 114, which is described later, so as to emit thermal electrons. The anode 142 generates X-rays when it receives electrons that are emitted by the cathode 141. The anode 142 is rotated due to the rotating magnetic field that is generated by the coil. The grid 143 is a structure that is provided on the circumference of the cathode 141. The grid 143 adjusts the potential gradient around the cathode 141 and switches on/off X-rays that are generated by the anode 142. The glass bulb 144 is a glass container that houses the cathode 141, the anode 142, and the grid 143.

The rotating-speed monitoring device 145 monitors the rotating speed of the anode 142. The method for monitoring the rotating speed of the anode 142 by the rotating-speed monitoring device 145 is not particularly limited. The rotating-speed monitoring device 145 uses for example lasers or infrared rays to measure the rotating speed of the anode 142 without being in contact with the anode 142. Alternatively, the rotating-speed monitoring device 145 measures oscillations of the anode 142 to measure the rotating speed of the anode 142. Alternatively, the rotating-speed monitoring device 145 calculates the rotating speed of the anode 142 by using the electric power that is supplied by the anode drive circuitry 16 to the X-ray tube 14 or its set value. The rotating-speed monitoring device 145 transmits the monitored rotating speed of the anode 142 to the processing circuitry 26, which is described later, as appropriate.

Figure 6:
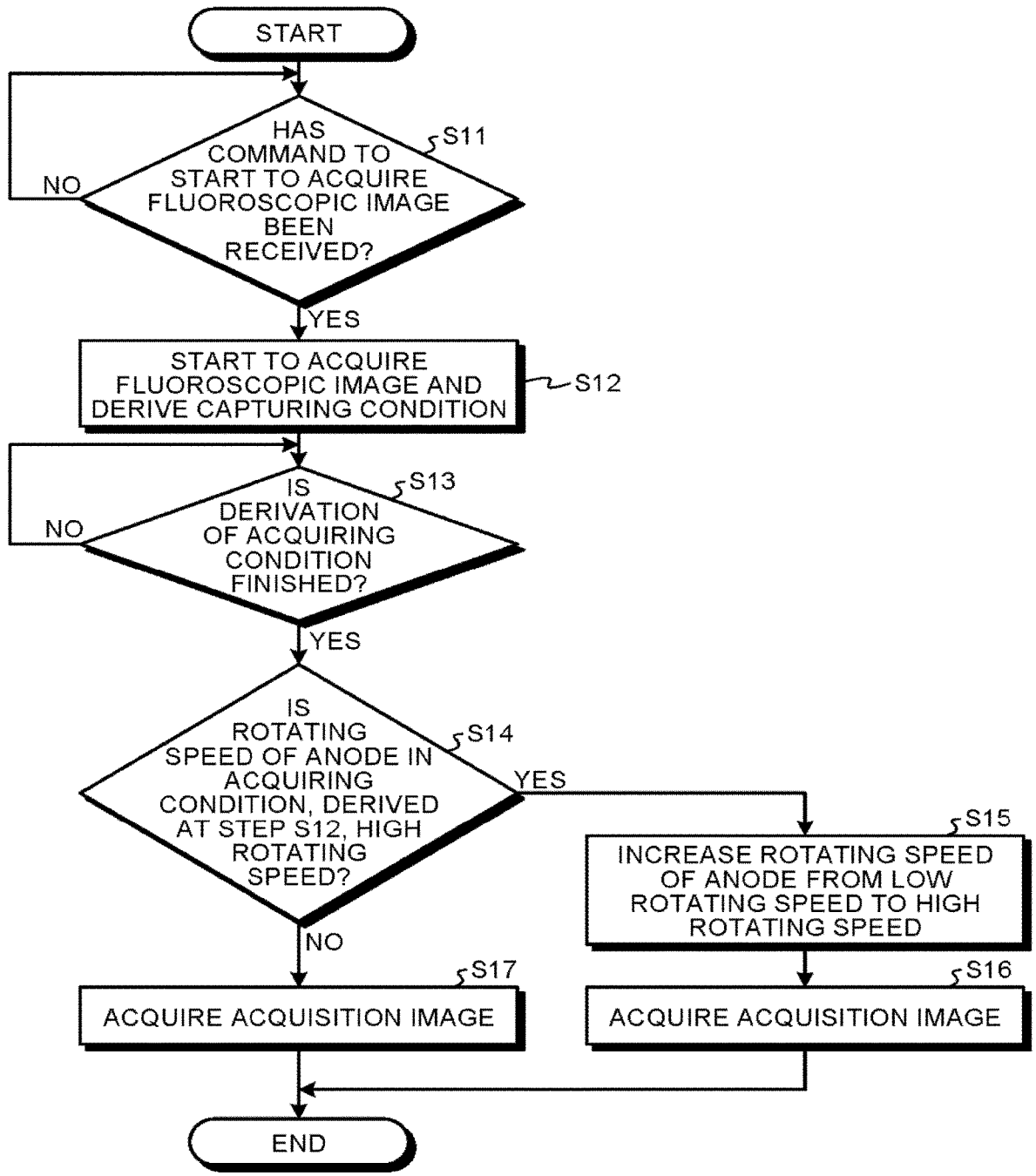
FIG. 6 is a flowchart that illustrates an example of the process that is performed by the X-ray diagnostic apparatus according to the first embodiment.
Figure 7:
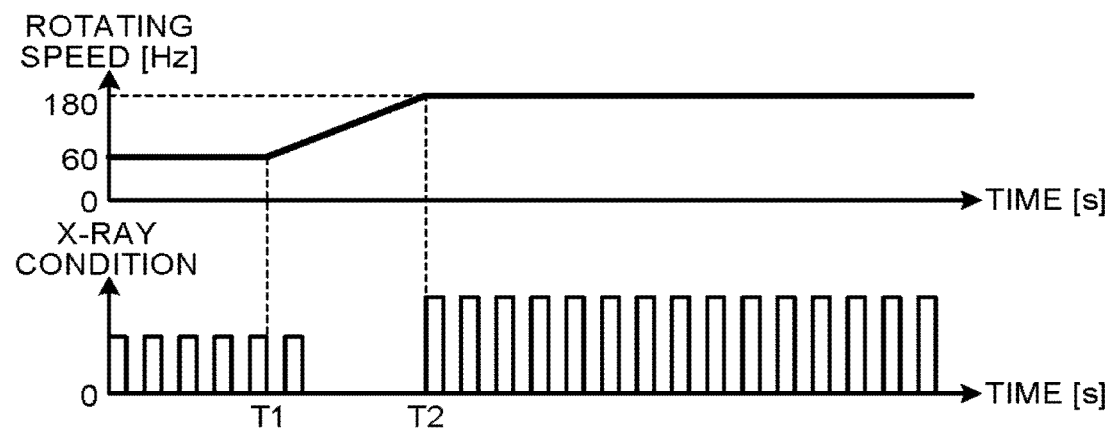
FIG. 7 is a diagram that illustrates an example of the case where the X-ray diagnostic apparatus according to the first embodiment acquires a fluoroscopic image, increases the rotating speed of the anode from the low rotating speed to the high rotating speed, and acquires an acquisition image.
Figure 8:
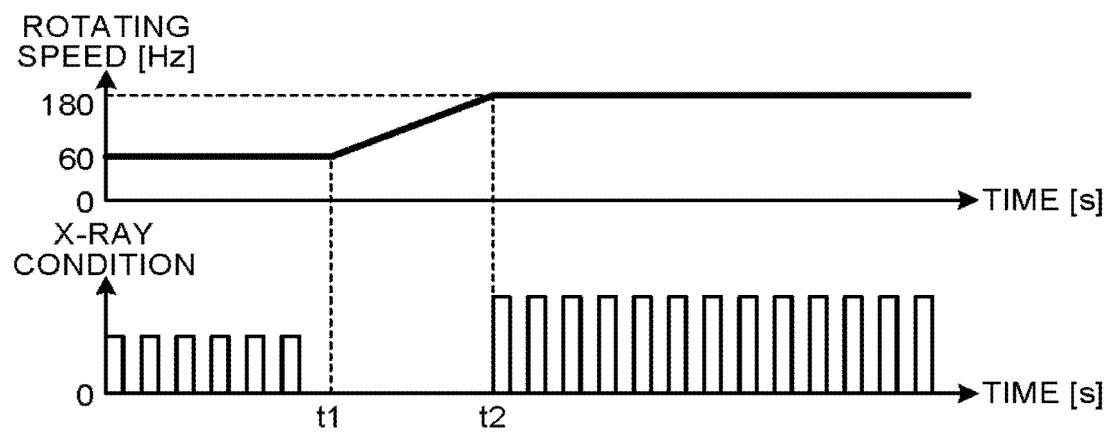
FIG. 8 is a diagram that illustrates an example of the case where the conventional X-ray diagnostic apparatus acquires a fluoroscopic image, increases the rotating speed of the anode from the low rotating speed to the high rotating speed, and acquires an acquisition image.

Next, with reference to FIGS. 6, 7, and 8, the process performed by the X-ray diagnostic apparatus 1 according to the first embodiment is explained. FIG. 6 is a flowchart that illustrates an example of the process that is performed by the X-ray diagnostic apparatus 1 according to the first embodiment. FIG. 7 is a diagram that illustrates an example of the case where the X-ray diagnostic apparatus 1 according to the first embodiment acquires a fluoroscopic image, increases the rotating speed of the anode from the low rotating speed to the high rotating speed, and acquires an acquisition image. FIG. 8 is a diagram that illustrates an example of the case where the conventional X-ray diagnostic apparatus acquires a fluoroscopic image, increases the rotating speed of the anode from the low rotating speed to the high rotating speed, and acquires an acquisition image.

While the X-ray diagnostic apparatus 1 is in operation, the processing circuitry 26 reads the program, which corresponds to the monitoring function 261, from the memory circuitry 25 and executes it to receive the rotating speed of the anode 142 from the rotating-speed monitoring device 145.

As illustrated in FIG. 6, the processing circuitry 26 reads the program, which corresponds to the control function 265, from the memory circuitry 25 and executes it to determine whether it has received a command to start to acquire a fluoroscopic image (Step S11). If a command for starting to acquire a fluoroscopic image has been received (Yes at Step S11), the processing circuitry 26 proceeds to the operation at Step S12. If a command for starting to acquire a fluoroscopic image has not been received (No at Step S11), the processing circuitry 26 stands by until a command for starting to acquire a fluoroscopic image is received. A command for starting to acquire a fluoroscopic image is input by for example a user who uses the input circuitry 21.

As illustrated in FIG. 6, the processing circuitry 26 reads the program, which corresponds to the image-acquiring control function 264, and the program, which corresponds to the derivation function 262, from the memory circuitry 25 and executes them to start to acquire a fluoroscopic image and derive an acquiring condition (Step S12). For example, as illustrated in FIG. 7, the X-ray diagnostic apparatus 1 derives an acquiring condition from a fluoroscopic image while it conducts pulsed fluoroscopy on the subject P. Alternatively, the X-ray diagnostic apparatus 1 derives an acquiring condition from a fluoroscopic image while it conducts continuous fluoroscopy on the subject P. Here, the acquiring condition is a condition under which the X-ray diagnostic apparatus 1 acquires acquisition images of the subject P. The acquiring condition is, for example, the rotating speed of the anode 142, the tube current, the tube voltage, the current that flows through the cathode 141, the electric potential of the grid 143, the positions of the aperture blades of the collimator 15, the position of the tabletop of the couch 13, or the arrangement of the C arm 18. Furthermore, the vertical axis in the lower diagram of FIG. 7 indicates the X-ray condition. Here, the X-ray condition means the tube voltage, the tube current, and the time during which X-rays are emitted. Furthermore, the same holds for the vertical axis in the lower diagram of FIGS. 8, 10, 11, and 12.

As illustrated in FIG. 6, the processing circuitry 26 reads the program, which corresponds to the rotating-speed control function 263, from the memory circuitry 25 and executes it to determine whether derivation of the acquiring condition is finished (Step S13). If derivation of the acquiring condition is finished (Yes at Step S13), the processing circuitry 26 proceeds to the operation at Step S14. If derivation of the acquiring condition is not finished (No at Step S13), the processing circuitry 26 stands by until derivation of the acquiring condition is finished. For example, the rotating-speed control function 263 determines that the derivation function 262 has finished deriving the acquiring condition by using the following method.

If variations in the statistic in the brightness of pixels of a fluoroscopic image satisfy a determination condition, the rotating-speed control function 263 determines that the derivation function 262 has finished deriving the acquiring condition. Here, for example, the determination condition is a condition such that the statistic falls within a predetermined range during more than a predetermined time. Here, the predetermined time and the predetermined range are the time and the range that are set before acquiring of fluoroscopic images of the subject P is started. The time and the range may be conditions that are set by a user, or they may be preset fixed conditions. Furthermore, the statistic is for example an average, variance, standard deviation, maximal value, minimum value, middle value, or mode value. Furthermore, the statistic, mentioned here, may be for example the amount that is defined by the user of the X-ray diagnostic apparatus 1 as needed.

The rotating-speed control function 263 may determine that the derivation function 262 has finished deriving the acquiring condition if an operating mechanism is stopped and variations in the statistic in the brightness of pixels of a fluoroscopic image satisfy the determination condition. Here, the operating mechanism is a component that is included in the components of the image acquisition apparatus 10 and that makes movement or deformation in accordance with the acquiring condition preparatory to image acquiring. Examples of the operating mechanism include the couch 13, on which the subject P is placed, the collimator 15 that adjusts the irradiation range of X-rays, or the C arm 18. Specifically, as the couch 13 moves the tabletop to adjust the position of the subject P preparatory to image acquiring, it is included in the operating mechanism. Furthermore, as the collimator 15 slides the aperture blades to control the X-rays irradiation range preparatory to image acquiring, it is included in the operating mechanism. Moreover, as the C arm 18 moves the X-ray tube 14, the collimator 15, or the X-ray detector 17 to control the irradiation angle of X-rays, or the like, it is included in the operating mechanism. Conversely, for example, although the anode 142 is a component that rotates and moves in accordance with an acquiring condition, it does not rotate or move preparatory to image acquiring; therefore, it is not included in the operating mechanism.

For example, if the couch 13, on which the subject P is placed, is stopped, the rotating-speed control function 263 determines that the derivation function 262 has finished deriving the acquiring condition. Furthermore, for example, if the collimator 15 is stopped, the rotating-speed control function 263 determines that the derivation function 262 has finished deriving the acquiring condition. This is because, if the couch 13 or the collimator 15 is stopped, it may be determined that the X-ray diagnostic apparatus 1 is making preparations to acquire acquisition images under the acquiring condition that is derived at Step S12 except for the rotating speed of the anode 142 and associated conditions. However, the rotating-speed control function 263 does not always determine whether the derivation function 262 has finished deriving the acquiring condition only on the basis of movements of the couch 13 or the collimator 15. Therefore, it is preferable that the rotating-speed control function 263 uses these methods in combination with the method of using the statistic in the brightness of pixels of a fluoroscopic image or other methods.

If the information indicating that the subject P has stopped breathing or the information indicating that the subject P has received a command to stop breathing is received, the rotating-speed control function 263 may determine that the derivation function 262 has finished deriving the acquiring condition. Furthermore, if the information indicating that the subject P has stopped moving or the information indicating that the subject P has received a command to stop moving is received, the rotating-speed control function 263 may determine that the derivation function 262 has finished deriving the acquiring condition. This is because, if the processing circuitry 26 has received the information, it may be determined that the X-ray diagnostic apparatus 1 is making preparations to acquire acquisition images under the acquiring condition that is derived at Step S12 except for the rotating speed of the anode 142 and associated conditions. However, the rotating-speed control function 263 does not always determine whether the derivation function 262 has finished deriving the acquiring condition only on the basis of whether the processing circuitry 26 has received the information. Therefore, it is preferable that the rotating-speed control function 263 uses these methods in combination with the method of using the statistic in the brightness of pixels of a fluoroscopic image or other methods. For example, the rotating-speed control function 263 determines that the derivation function 262 has finished deriving the acquiring condition if the information indicating that the subject P has stopped breathing or the information indicating that the subject P has received a command to stop breathing is received and if variations in the statistic in the brightness of pixels of a fluoroscopic image satisfy the determination condition. Furthermore, for example, the rotating-speed control function 263 determines that the derivation function 262 has finished deriving the acquiring condition if the information indicating that the subject P has stopped moving or the information indicating that the subject P has received a command to stop moving is received and if variations in the statistic in the brightness of pixels of a fluoroscopic image satisfy the determination condition.

The rotating-speed control function 263 may determine that the derivation function 262 has finished deriving the acquiring condition if the user has performed a predetermined operation. The predetermined operation, mentioned here, is an operation that is frequently performed when an acquisition image of a specific site of the subject P is acquired by using a specific method. This is because, if such an operation is performed, it may be determined that the X-ray diagnostic apparatus 1 is making preparations to acquire acquisition images under the acquiring condition that is derived at Step S12 except for the rotating speed of the anode 142 and associated conditions. Here, the predetermined operation is an operation that is set before acquiring of a fluoroscopic image of the subject P is started. This operation may be a condition that is set by the user, or it may be a preset fixed condition. However, the rotating-speed control function 263 does not always determine whether the derivation function 262 has finished deriving the acquiring condition only on the basis of whether such an operation is performed. Therefore, it is preferable that the rotating-speed control function 263 uses this method in combination with the method of using the statistic in the brightness of pixels of a fluoroscopic image or other methods. For example, the rotating-speed control function 263 determines that the derivation function 262 has finished deriving the acquiring condition if the user has performed the predetermined operation and if variations in the statistic in the brightness of pixels of a fluoroscopic image satisfy the determination condition.

The rotating-speed control function 263 may determine that the derivation function 262 has finished deriving the acquiring condition if a predetermined time has elapsed after the X-ray tube 14 has started to emit X-rays to acquire fluoroscopic images. This is because, although the time it takes from the start of fluoroscopy to derivation of the acquiring condition is not the same during each examination, it is often nearly equal. Here, the predetermined time is a time that is set before acquiring of fluoroscopic images of the subject P is started. The time may be a condition that is set by the user, or it may be a preset fixed condition. The predetermined time, mentioned here, is for example 3 seconds. However, the rotating-speed control function 263 does not always determine whether the derivation function 262 has finished deriving the acquiring condition only on the basis of whether a predetermined time has elapsed after fluoroscopy has been started. Therefore, it is preferable that the rotating-speed control function 263 uses this method in combination with the method of using the statistic in the brightness of pixels of a fluoroscopic image or other methods. For example, the rotating-speed control function 263 determines that the derivation function 262 has finished deriving the acquiring condition if a predetermined time has elapsed after the X-ray tube 14 has started to emit X-rays to acquire fluoroscopic images and if variations in the statistic in the brightness of pixels of a fluoroscopic image satisfy the determination condition.

The rotating-speed control function 263 may determine that the derivation function 262 has finished deriving the acquiring condition if the user satisfies the position condition. Here, the position condition is set as, for example, an area where the user can be located when acquiring of acquisition images is started. For example, if the user stands within the area that is set as the position condition, the rotating-speed control function 263 determines that the position condition is satisfied. Furthermore, the rotating-speed control function 263 may acquire the position of the user from images that are acquired by using for example an optical camera. The position condition may be set on the basis of, for example, the position where the user is often located when acquiring of acquisition images is started during previous examinations. Furthermore, the position condition may be a condition that is set by the user, or it may be a preset condition (a certain range from the console 20, or the like). Moreover, it is preferable that the rotating-speed control function 263 uses this method in combination with the method of using the statistic in the brightness of pixels of a fluoroscopic image or other methods. For example, the rotating-speed control function 263 determines that the derivation function 262 has finished deriving the acquiring condition if the user satisfies the position condition and if variations in the statistic in the brightness of pixels of a fluoroscopic image satisfy the determination condition.

As illustrated in FIG. 6, the processing circuitry 26 reads the program, which corresponds to the rotating-speed control function 263, from the memory circuitry 25 and executes it to determine whether the rotating speed of the anode 142 in the acquiring condition, derived at Step S12, is the high rotating speed (Step S14). If the rotating speed of the anode 142 in the acquiring condition, derived at Step S12, is the high rotating speed (Yes at Step S14), the processing circuitry 26 proceeds to the operation at Step S15. If the rotating speed of the anode 142 in the acquiring condition, derived at Step S12, is not the high rotating speed (No at Step S14), the processing circuitry 26 proceeds to the operation at Step S17. That is, if the rotating speed of the anode 142 in the acquiring condition, derived at Step S12, is the low rotating speed, the processing circuitry 26 proceeds to the operation at Step S17. Furthermore, as illustrated in FIG. 7, for example, the low rotating speed is 60 Hz, and the high rotating speed is 180 Hz.

As illustrated in FIGS. 6 and 7, the processing circuitry 26 reads the program, which corresponds to the rotating-speed control function 263, from the memory circuitry 25 and executes it to increase the rotating speed of the anode 142 from the low rotating speed to the high rotating speed (Step S15). Specifically, the processing circuitry 26 uses the rotating-speed control function 263 to start to increase the rotating speed of the anode 142 from the low rotating speed to the high rotating speed at the interval from when the derivation function 262 finishes deriving the acquiring condition to when the X-ray tube 14 finishes emitting X-rays to acquire fluoroscopic images. For example, if the operation at Step S14 is finished at a time T1, illustrated in FIG. 7, the processing circuitry 26 starts to increase the rotating speed of the anode 142 from the low rotating speed to the high rotating speed at the time T1. If the rotating speed of the anode 142 reaches the high rotating speed, the processing circuitry 26 proceeds to the operation at Step S16. For example, if the rotating speed of the anode 142 reaches the high rotating speed at a time T2, illustrated in FIG. 7, the processing circuitry 26 proceeds to the operation at Step S16 at the time T2.

As illustrated in FIGS. 6 and 7, the processing circuitry 26 reads the program, which corresponds to the image-acquiring control function 264, from the memory circuitry 25 and executes it to acquire an acquisition image (Step S16). In this case, the rotating speed of the anode 142 is 180 Hz. Specifically, the processing circuitry 26 uses the image-acquiring control function 264 to start image acquiring in the interval from when the rotating speed of the anode 142, monitored by the monitoring function 261, reaches the high rotating speed to when the time, which equals to the time necessary to increase the low rotating speed to the high rotating speed by the rotating-speed control function 263, elapses after the starting point of reckoning, that is, after the X-ray tube 14 finishes emitting X-rays to acquire fluoroscopic images. For example, as illustrated in FIG. 7, the processing circuitry 26 starts to acquire an acquisition image at the time T2 in which the rotating speed of the anode 142 reaches the high rotating speed. If acquiring of acquisition images is finished, the processing circuitry 26 terminates the process.

As illustrated in FIG. 6, the processing circuitry 26 reads the program, which corresponds to the image-acquiring control function 264, from the memory circuitry 25 and executes it to acquire an acquisition image (Step S17). In this case, the rotating speed of the anode 142 is 60 Hz. If acquiring of acquisition images is finished, the processing circuitry 26 terminates the process.

An explanation is given above of a case where the rotating speed of the anode 142 is started to increase to the high rotating speed if it is determined that the acquiring condition has been derived. Specifically, an explanation is given of a case where the rotating speed of the anode 142 is started to increase if variations in the statistic in the brightness of pixels of a fluoroscopic image satisfy the determination condition, if the operating mechanism is stopped, if the information indicating that the subject P has stopped breathing or the information indicating that the subject P has received a command to stop breathing is received, if the information indicating that the subject P has stopped moving or the information indicating that the subject P has received a command to stop moving is received, if the user has performed a predetermined operation, if a predetermined time has elapsed after the X-ray tube 14 has started to emit X-rays to acquire fluoroscopic images, or if the user satisfies the position condition. However, this is not a limitation on the embodiment.

For example, there may be a case where the processing circuitry 26 determines the time in which the rotating speed of the anode 142 is started to increase by using the state information that indicates the state of examination and starts to increase the rotating speed of the anode 142 at the determined time. Here, the state information is at least one of for example the information that indicates variations in the statistic in the brightness of pixels of a fluoroscopic image, the information that indicates whether the operating mechanism is stopped, the information that indicates whether the subject has stopped breathing, the information that indicates whether the subject has received a command to stop breathing, the information that indicates whether the subject has stopped moving, the information that indicates whether the subject has received a command to stop moving, the information that indicates whether the user has performed a predetermined operation, the information that indicates the time that has elapsed after the X-ray tube 14 has started to emit X-rays to acquire fluoroscopic images, and the information that indicates the position of the user.

An explanation is given below of an example of the process by the processing circuitry 26 to determine the time when the rotating speed of the anode 142 is started to increase by using the state information. First, the processing circuitry 26 acquires the combination of the state information at the time when the rotating speed of the anode 142 is started to increase and the evaluation of the time when the rotating speed of the anode 142 is started to increase. Here, the processing circuitry 26 acquires this combination each time an examination is conducted.

The state information at the time when the rotating speed of the anode 142 is started to increase is, for example, the information that indicates variations in the statistic in the brightness of pixels of a fluoroscopic image (e.g., a differential value of standard deviation in brightness) at the time when the rotating speed of the anode 142 is started to increase. Furthermore, for example, the state information at the time when the rotating speed of the anode 142 is started to increase is the information that indicates whether the operating mechanism is stopped, whether the subject has stopped breathing, whether the subject has received a command to stop breathing, whether the subject has stopped moving, whether the subject has received a command to stop moving, whether the user has performed a predetermined operation, whether a predetermined time has elapsed after the X-ray tube 14 has started to emit X-rays to acquire fluoroscopic images, whether the user satisfies the position condition, or the like, at the time when the rotating speed of the anode 142 is started to increase.

Furthermore, the evaluation of the time when the rotating speed of the anode 142 is started to increase is an evaluation that indicates how appropriate the time when the rotating speed of the anode 142 is started to increase is in terms of prompt start of acquiring of acquisition images. Hereafter, the evaluation of the time when the rotating speed of the anode 142 is started to increase is sometimes simply referred to as the evaluation. For example, the processing circuitry 26 acquires, as an evaluation, the difference between the time when the rotating speed of the anode 142 reaches the high rotating speed and the start time of image acquiring. For example, the processing circuitry 26 acquires the difference between the time when the rotating speed of the anode 142 reaches the high rotating speed and the start time of image acquiring, which is the time when the user performs an input operation indicating the start of image acquiring via the input circuitry 21.

For example, if the user performs an input operation indicating the start of image acquiring before the rotating speed of the anode 142 reaches the high rotating speed, the processing circuitry 26 may make the evaluation that the time when the rotating speed of the anode 142 is started to increase is too late. This is because, in this case, it may be estimated that if the rotating speed of the anode 142 is started to increase earlier, acquiring of an acquisition image may be started more promptly. Furthermore, for example, if it takes a long time from when the rotating speed of the anode 142 reaches the high rotating speed to when image acquiring is started, the processing circuitry 26 may make the evaluation that the time when the rotating speed of the anode 142 is started to increase is too early. This is because, in this case, it may be estimated that even if the time when the rotating speed of the anode 142 is started to increase is delayed more, the start time of acquiring of acquisition images is not affected. Therefore, the processing circuitry 26 acquires the evaluation that it is more appropriate as the time when the rotating speed of the anode 142 is started to increase if the difference between the time when the rotating speed of the anode 142 reaches the high rotating speed and the start time of image acquiring is smaller.

Next, the processing circuitry 26 calculates the weighting coefficient for each piece of state information on the basis of the acquired evaluation. For example, the processing circuitry 26 acquires the combination of the state information at the time when the rotating speed of the anode 142 is started to increase and the evaluation with regard to multiple examinations, and it compares the acquired combinations with each other to acquire the degree of correlation between each piece of state information and an evaluation. For example, the processing circuitry 26 acquires, as the degree of correlation, the correlation coefficient between the variation in the statistic in the brightness of pixels of a fluoroscopic image at the time when the rotating speed of the anode 142 is started to increase and the evaluation. Furthermore, for example, the processing circuitry 26 acquires, as the degree of correlation, the difference between the average value of evaluations in a case where the operating mechanism is stopped at the time when the rotating speed of the anode 142 is started to increase and the average value of evaluations in a case where the operating mechanism is not stopped at the time when the rotating speed of the anode 142 is started to increase. Then, for each piece of state information, the processing circuitry 26 calculates the weighting coefficient for each piece of state information in accordance with the degree of correlation with the evaluation.

Here, an explanation is given of a case where an examination E1 is further conducted after a weighting coefficient is calculated for each piece of state information. The processing circuitry 26 determines the time when the rotating speed of the anode 142 is started to increase during the examination E1 on the basis of the state information indicating the state of the examination E1 and the weighting coefficient. Specifically, the processing circuitry 26 receives an input of the state information, which indicates variations in the statistic in the brightness of pixels of a fluoroscopic image or whether the operating mechanism is stopped, in real time and performs calculations on the input state information by using the weighting coefficient, thereby determining the time when the rotating speed of the anode 142 is started to increase. Then, the processing circuitry 26 starts to increase the rotating speed of the anode 142 at the determined time.

Here, the processing circuitry 26 further acquires the evaluation of the time when the rotating speed of the anode 142 is started to increase during the examination E1. Furthermore, the processing circuitry 26 uses the acquired evaluation and the state information, which indicates the state of the examination E1 at the time when the rotating speed of the anode 142 starts to increase, to change the weighting coefficient for each piece of state information. In other words, each time an examination is conducted, the processing circuitry 26 learns the weighting coefficient for each piece of state information in the relationship between the state information at the time when the rotating speed of the anode 142 is started to increase and the evaluation of the time when the rotating speed of the anode 142 is started to increase. Furthermore, if an examination is further conducted, the processing circuitry 26 may determine the time when the rotating speed of the anode 142 is started to increase on the basis of the state information in the examination and the learnt weighting coefficient and start to increase the rotating speed of the anode 142 at the determined time.

The X-ray diagnostic apparatus 1 according to the first embodiment is explained above. In accordance with the derived acquiring condition, the rotating-speed control function 263 starts to increase the rotating speed of the anode 142 from the low rotating speed to the high rotating speed before the X-ray tube 14 finishes emitting X-rays to acquire fluoroscopic images. Then, the image-acquiring control function 264 starts to acquire acquisition images in the interval from when the rotating speed of the anode 142 reaches the high rotating speed to when the time necessary to increase the low rotating speed to the high rotating speed elapses after the X-ray tube 14 finishes emitting X-rays to acquire fluoroscopic images.

Conversely, as illustrated in FIG. 8, the conventional X-ray diagnostic apparatus starts to increase the rotating speed of the anode 142 from the low rotating speed to the high rotating speed at a time t1 in which the X-ray tube finishes emitting X-rays to acquire fluoroscopic images. Then, as illustrated in FIG. 8, the conventional X-ray diagnostic apparatus starts to acquire acquisition images after a time t2 in which the time necessary to increase the low rotating speed to the high rotating speed elapses after the X-ray tube finishes emitting X-rays to acquire fluoroscopic images.

That is, the X-ray diagnostic apparatus 1 according to the first embodiment may start to acquire acquisition images more promptly than the conventional X-ray diagnostic apparatus.

Furthermore, if the processing circuitry 26 does not derive an acquiring condition from a fluoroscopic image at Step S12, the condition for acquiring acquisition images by the X-ray diagnostic apparatus 1 is previously set. In this case, if a predetermined time has elapsed after acquiring of fluoroscopic images has been started, the processing circuitry 26 does not perform the operations at Step S13 and Step S14, and it proceeds to the operation at Step S15 or Step S17 in accordance with the previously set condition.

The X-ray diagnostic apparatus 1 according to the first embodiment does not acquire acquisition images from when the derivation function 262 finishes deriving the acquiring condition to when the rotating speed of the anode 142, monitored by the monitoring function 261, reaches the high rotating speed. Conversely, an X-ray diagnostic apparatus according to the second embodiment acquires acquisition images from when the derivation function 262 finishes deriving the acquiring condition to when the rotating speed of the anode 142, monitored by the monitoring function 261, reaches the high rotating speed. Here, the same reference numerals as those used in the explanation of the first embodiment are used in the explanation of the second embodiment, and duplicated explanations are appropriately omitted.

Figure 9:
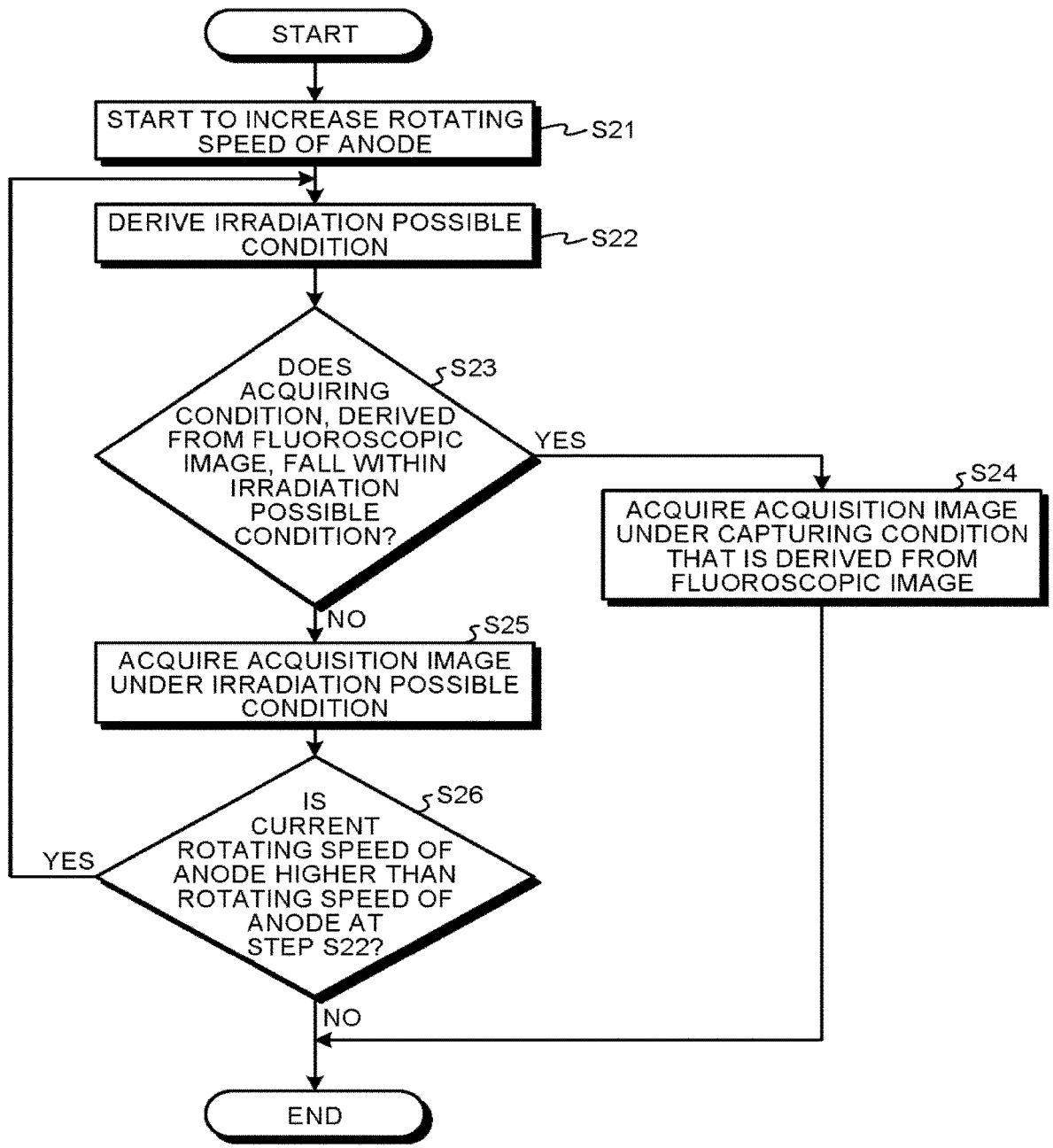
FIG. 9 is a flowchart that illustrates an example of the process that is performed by the X-ray diagnostic apparatus according to a second embodiment.
Figure 10:
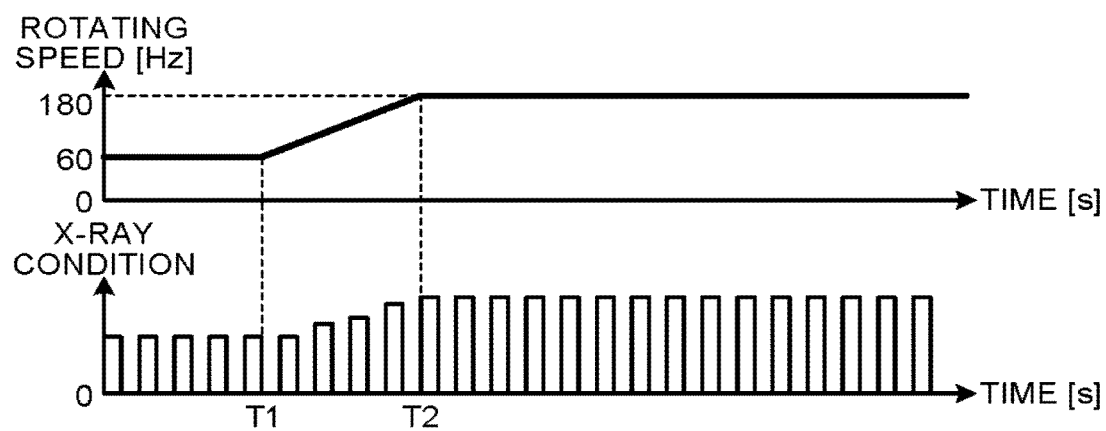
FIG. 10 is a diagram that illustrates an example of the case where the X-ray diagnostic apparatus according to the second embodiment acquires a fluoroscopic image and then increases the rotating speed of the anode from the low rotating speed to the high rotating speed while it acquires an acquisition image.

With reference to FIGS. 9 and 10, an explanation is given of the process that is performed by the X-ray diagnostic apparatus 1 according to the second embodiment. FIG. 9 is a flowchart that illustrates an example of the process that is performed by the X-ray diagnostic apparatus according to the second embodiment. FIG. 10 is a diagram that illustrates an example of the case where the X-ray diagnostic apparatus according to the second embodiment acquires a fluoroscopic image and then increases the rotating speed of the anode from the low rotating speed to the high rotating speed while it acquires an acquisition image.

While the X-ray diagnostic apparatus 1 is in operation, the processing circuitry 26 reads the program, which corresponds to the monitoring function 261, from the memory circuitry 25 and executes it to receive the rotating speed of the anode 142 from the rotating-speed monitoring device 145.

As illustrated in FIGS. 9 and 10, the processing circuitry 26 reads the program, which corresponds to the rotating-speed control function 263, from the memory circuitry 25 and executes it to start to increase the rotating speed of the anode 142 (Step S21). For example, as illustrated in FIGS. 9 and 10, the processing circuitry 26 derives an acquiring condition from the fluoroscopic image and then starts to increase the rotating speed of the anode 142 from the low rotating speed to the high rotating speed.

As illustrated in FIG. 9, the processing circuitry 26 reads the program, which corresponds to the derivation function 262, from the memory circuitry 25 and executes it to derive an irradiation possible condition (Step S22). The irradiation possible condition is for example the condition for acquisition image acquiring that may be achieved by using the rotating speed of the anode 142 that is monitored by the monitoring function 261 at present. The irradiation possible condition is, for example, the tube current, the tube voltage, the current that flows through the cathode 141, the electric potential of the grid 143, the positions of the aperture blades of the collimator 15, the position of the tabletop of the couch 13, or the arrangement of the C arm 18.

As illustrated in FIG. 9, the processing circuitry 26 reads the program, which corresponds to the image-acquiring control function 264, from the memory circuitry 25 and executes it to determine whether the acquiring condition, derived from the fluoroscopic image, falls within the irradiation possible condition (Step S23). Specifically, the processing circuitry 26 uses the image-acquiring control function 264 to determine whether the X-ray diagnostic apparatus 1 may conduct acquiring of acquisition images under the acquiring condition, derived from the fluoroscopic image, by using the current rotating speed of the anode 142. If the acquiring condition, derived from the fluoroscopic image, falls within the irradiation possible condition (Yes at Step S23), the processing circuitry 26 proceeds to the operation at Step S24. If the acquiring condition, derived from the fluoroscopic image, does not fall within the irradiation possible condition (No at Step S23), the processing circuitry 26 proceeds to the operation at Step S25. Furthermore, the acquiring condition mentioned here is the acquiring condition that is explained in the first embodiment.

As illustrated in FIGS. 9 and 10, the processing circuitry 26 reads the program, which corresponds to the image-acquiring control function 264, from the memory circuitry 25 and executes it to acquire an acquisition image under the acquiring condition that is derived from the fluoroscopic image (Step S24). If acquiring of the acquisition image is finished, the processing circuitry 26 terminates the process.

As illustrated in FIGS. 9 and 10, the processing circuitry 26 reads the program, which corresponds to the image-acquiring control function 264, from the memory circuitry 25 and executes it to acquire an acquisition image under the irradiation possible condition (Step S25). If acquiring of the acquisition image is finished, the processing circuitry 26 proceeds to the operation at Step S26.

As illustrated in FIG. 9, the processing circuitry 26 reads the program, which corresponds to the rotating-speed control function 263, and executes it to determine whether the current rotating speed of the anode 142 is higher than the rotating speed of the anode 142 at Step S22 (Step S26). If the current rotating speed of the anode 142 is higher than the rotating speed of the anode 142 at Step S22 (Yes at Step S26), the processing circuitry 26 proceeds to the operation at Step S22. If the current rotating speed of the anode 142 is the same as the rotating speed of the anode 142 at Step S22 (No at Step S26), the processing circuitry 26 terminates the process. Furthermore, in this case, the rotating speed of the anode 142 has reached the high rotating speed.

The X-ray diagnostic apparatus 1 according to the second embodiment has been explained above. The derivation function 262 derives the irradiation possible condition that may be achieved by using the rotating speed of the anode 142 that is monitored by the monitoring function 261. If the acquiring condition does not fall within the irradiation possible condition, the image-acquiring control function 264 acquires acquisition images under the irradiation possible condition. Therefore, the X-ray diagnostic apparatus 1 may starts to acquire acquisition images before the rotating speed of the anode 142, monitored by the monitoring function 261, reaches the high rotating speed.

Conversely, as illustrated in FIG. 8, the conventional X-ray diagnostic apparatus does not acquire acquisition images from the time t1, at which the X-ray tube finishes emitting X-rays to acquire fluoroscopic images, to the time t2, at which the rotating speed of the anode 142 reaches the high rotating speed. Therefore, as illustrated in FIG. 8, the conventional X-ray diagnostic apparatus may starts to acquire acquisition images only after the time t2 at which the rotating speed of the anode reaches the high rotating speed.

That is, the X-ray diagnostic apparatus 1 according to the second embodiment may starts to acquire acquisition images promptly as compared to conventional X-ray diagnostic apparatuses.

Figure 11:
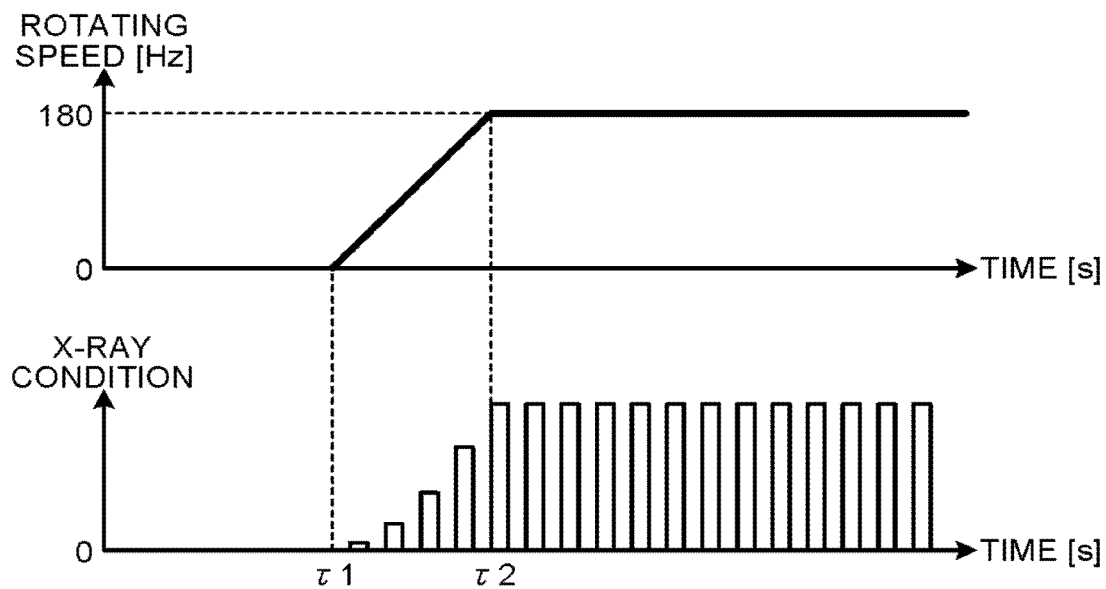
FIG. 11 is a diagram that illustrates an example of the case where the X-ray diagnostic apparatus according to the second embodiment increases the rotating speed of the anode from the stopped state to the high rotating speed while it acquires an acquisition image.

An explanation is given of a case where, after a fluoroscopic image is acquired, the rotating speed of the anode 142 is started to increase and simultaneously an acquisition image is acquired under the irradiation possible condition; however, this is not a limitation on the embodiment. As illustrated in FIG. 11, for example, the X-ray diagnostic apparatus 1 according to the second embodiment may acquire acquisition images under the irradiation possible condition if the acquiring condition, derived from the fluoroscopic image, does not fall within the irradiation possible condition from a time t1 when the rotating speed of the anode 142 is started to increase from the stopped state to the high rotating speed until a time t2 when the rotating speed of the anode 142 reaches the high rotating speed.

Alternatively, for example, the X-ray diagnostic apparatus 1 according to the second embodiment may acquire acquisition images under the irradiation possible condition if the acquiring condition, derived from the fluoroscopic image, does not fall within the irradiation possible condition from the time when the rotating speed of the anode 142 starts to increase from the stopped state to the low rotating speed until the time when the rotating speed of the anode 142 reaches the high rotating speed.

In these cases, the X-ray diagnostic apparatus 1 performs the same process as that is explained with reference to FIG. 9. However, in these cases, the acquiring condition is previously set, and the processing circuitry 26 starts to increase the rotating speed of the anode 142 from the stopped state to the high rotating speed at Step S21. Therefore, the X-ray diagnostic apparatus 1 may start to acquire acquisition images even before the rotating speed of the anode 142, monitored by the monitoring function 261, reaches the high rotating speed.

Figure 12:
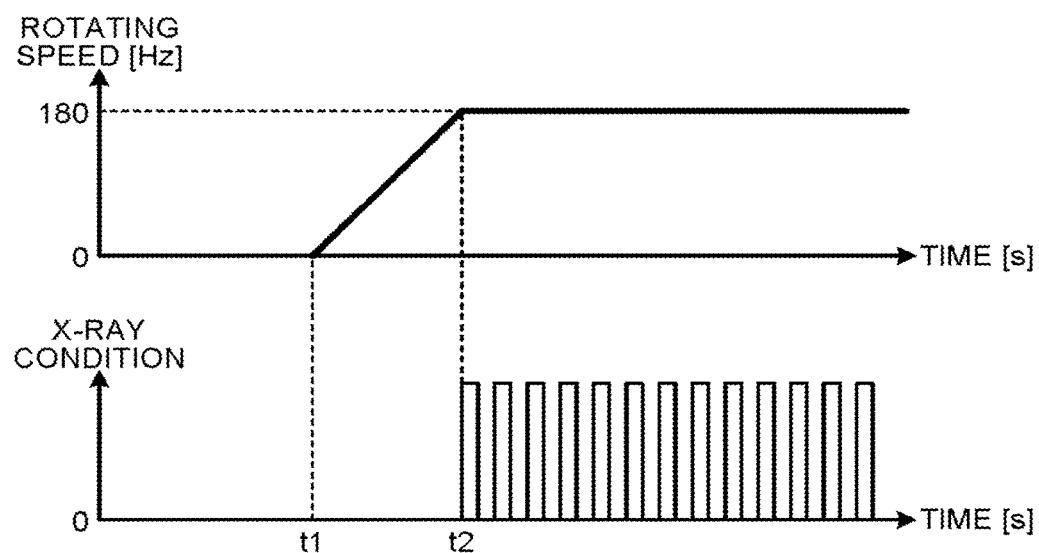
FIG. 12 is a diagram that illustrates an example of the case where the conventional X-ray diagnostic apparatus increases the rotating speed of the anode from the stopped state to the high rotating speed and acquires an acquisition image.

Conversely, as illustrated in FIG. 12, the conventional X-ray diagnostic apparatus does not acquire acquisition images from the time t1 when the rotating speed of the anode is started to increase from the stopped state to the high rotating speed until the time t2 when the rotating speed of the anode reaches the high rotating speed. Therefore, as illustrated in FIG. 12, the conventional X-ray diagnostic apparatus may start to acquire acquisition images only after the time t2 when the rotating speed of the anode reaches the high rotating speed.

That is, the X-ray diagnostic apparatus 1 according to the second embodiment may start to acquire acquisition images promptly as compared to conventional X-ray diagnostic apparatuses even in a case where the rotating speed of the anode 142 is increased from the stopped state to the high rotating speed.

An X-ray diagnostic apparatus according to a third embodiment decreases the rotating speed of the anode if the rotating speed of the anode, monitored by the monitoring function, is a rotating speed at which the anode resonates. Furthermore, the same reference numerals as those used in the explanations of the first embodiment and the second embodiment are used in the explanation of the third embodiment, and duplicated explanations are omitted as appropriate.

Figure 13:
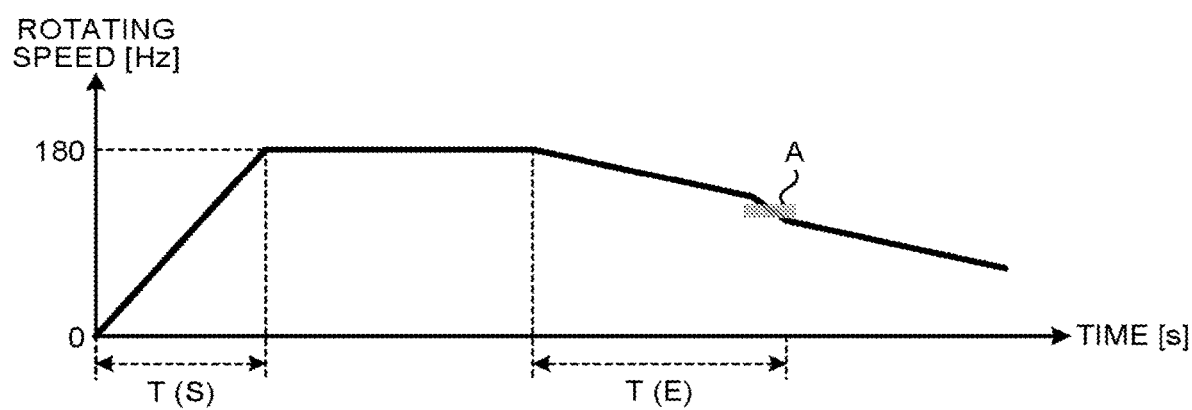
FIG. 13 is a diagram that illustrates an example of the case where the X-ray diagnostic apparatus according to a third embodiment decreases the rotating speed of the anode from the high rotating speed to the stopped state while it applies a brake to the anode.

With reference to FIG. 13, the X-ray diagnostic apparatus 1 according to the third embodiment is explained. FIG. 13 is a diagram that illustrates an example of the case where the X-ray diagnostic apparatus according to the third embodiment applies a brake to the anode while the rotating speed of the anode is decreased from the high rotating speed to the stopped state.

As illustrated in FIG. 13, the X-ray diagnostic apparatus 1 increases the rotating speed of the anode 142 from the stopped state to the high rotating speed during the time T(S), acquires an acquisition image, and decreases the rotating speed of the anode 142 from the high rotating speed to the stopped state. As illustrated in FIG. 13, the processing circuitry 26 performs the following operation when the rotating speed of the anode 142 is decreased from the high rotating speed to the stopped state.

While the X-ray diagnostic apparatus 1 is in operation, the processing circuitry 26 reads the program, which corresponds to the monitoring function 261, from the memory circuitry 25 and executes it to receive the rotating speed of the anode 142 from the rotating-speed monitoring device 145. The processing circuitry 26 reads the program, which corresponds to the rotating-speed control function 263, from the memory circuitry 25 and executes it to decrease the rotating speed of the anode 142 if the rotating speed of the anode 142, monitored by the monitoring function 261, is a rotating speed at which the anode 142 resonates.

Specifically, if the rotating speed of the anode 142, monitored by the monitoring function 261, is a rotating speed at which the anode 142 resonates, the processing circuitry 26 applies a brake to the rotation of the anode 142. The processing circuitry 26 uses the rotating-speed control function 263 to control the anode drive circuitry 16 so as to control the current that flows through the coil, which generates the rotating magnetic field, thereby applying a brake to the rotation of the anode 142. This allows the processing circuitry 26 to shorten the time during which the rotating speed of the anode 142 is the rotating speed at which the anode resonates, as indicated by the area A in FIG. 13.

The X-ray diagnostic apparatus 1 according to the third embodiment decreases the rotating speed of the anode 142 if the rotating speed of the anode 142, monitored by the monitoring function 261, is a rotating speed at which the anode 142 resonates. Therefore, the X-ray diagnostic apparatus 1 may reduce the energy that is necessary to apply a brake to the anode 142.

Furthermore, the processing circuitry 26 does not apply a brake to the rotation of the anode 142 if the rotating speed of the anode 142, monitored by the monitoring function 261, is not a rotating speed at which the anode 142 resonates. Specifically, if the rotating speed of the anode 142, monitored by the monitoring function 261, is not a rotating speed at which the anode 142 resonates, the processing circuitry 26 rotates the anode 142 through inertia during a time that is longer than the time T(E), which is illustrated in FIG. 13.

Thus, the X-ray diagnostic apparatus 1 according to the third embodiment may cause the rotating speed of the anode 142 to promptly reach the rotating speed at which acquisition images can be acquired again and may promptly start to acquiring acquisition images. Here, the rotating speed at which acquisition images can be acquired is for example the high rotating speed or the low rotating speed. Alternatively, the X-ray diagnostic apparatus 1 may cause the rotating speed of the anode 142 to promptly reach the rotating speed at which fluoroscopic images can be acquired again and may promptly start to acquire fluoroscopic images. Here, the rotating speed at which fluoroscopic images can be acquired is for example the low rotating speed. Furthermore, the X-ray diagnostic apparatus 1 may prevent the coil, which applies a brake to the anode 142, and the anode drive circuitry 16 from being heated more than necessary.

Although the first to third embodiments have been explained above, various different embodiments may be implemented other than the above-described embodiments.

In the above-described embodiments, the X-ray diagnostic apparatus 1 is explained. That is, an explanation is given of a case where the processing circuitry 26, included in the X-ray diagnostic apparatus 1, derives the acquiring condition from a fluoroscopic image and starts to increase the rotating speed of the anode 142 in accordance with the derived acquiring condition. However, this is not a limitation on the embodiment. For example, there may be a case where a medical-information processing apparatus, which is connected to the X-ray diagnostic apparatus 1, calculates the time when the rotating speed of the anode 142 is started to increase in the X-ray diagnostic apparatus 1 and notifies the calculated time to the X-ray diagnostic apparatus 1.

For example, the medical-information processing apparatus, which is connected to the X-ray diagnostic apparatus 1, first acquires the acquiring condition based on a fluoroscopic image. For example, the medical-information processing apparatus acquires fluoroscopic images, which are acquired by the X-ray diagnostic apparatus 1, via a network, or the like, and derives an acquiring condition from the acquired fluoroscopic images. Furthermore, according to another example, the X-ray diagnostic apparatus 1 derives an acquiring condition from the acquired fluoroscopic images, and the medical-information processing apparatus acquires the acquiring condition, derived by the X-ray diagnostic apparatus 1, via a network, or the like.

Next, the medical-information processing apparatus calculates the time when the rotating speed of the anode 142 in the X-ray diagnostic apparatus 1 is started to increase from the low rotating speed to the high rotating speed in accordance with the acquired acquiring condition, and it notifies the calculated time to the X-ray diagnostic apparatus 1.

For example, the medical-information processing apparatus acquires fluoroscopic images, acquired by the X-ray diagnostic apparatus 1, in real time and notifies the X-ray diagnostic apparatus 1 of the time when variations in the statistic in the brightness of pixels of the fluoroscopic image satisfy the determination condition as the time when the rotating speed of the anode 142 is started to increase. Furthermore, for example, the medical-information processing apparatus notifies the X-ray diagnostic apparatus 1 of, as the time when the rotating speed of the anode 142 is started to increase, the time when variations in the statistic in the brightness of pixels of the fluoroscopic image satisfy the determination condition and when at least one of the following conditions is satisfied: the operating mechanism is stopped, the subject P has stopped breathing, the subject P has received a command to stop breathing, the subject P has stopped moving, the subject P has received a command to stop moving, the user has performed a predetermined operation, a predetermined time has elapsed after the X-ray tube 14 has started to emit X-rays to acquire fluoroscopic images, and the user satisfies the position condition. Then, after receiving the notification, the X-ray diagnostic apparatus 1 starts to increase the rotating speed of the anode 142 to the high rotating speed at the notified time. Furthermore, if the notified time is the current time or the past time, the X-ray diagnostic apparatus 1 starts to increase the rotating speed of the anode 142 as soon as a notification is received.

Furthermore, for example, the medical-information processing apparatus calculates the time when the rotating speed of the anode 142 is started to increase on the basis of the state information during an examination and the learned weighting coefficient and notifies the X-ray diagnostic apparatus 1 of the calculated time as the time when the rotating speed of the anode 142 is started to increase. Then, after receiving a notification, the X-ray diagnostic apparatus 1 starts to increase the rotating speed of the anode 142 from the low rotating speed to the high rotating speed.

Here, there may be a case where the medical-information processing apparatus is connected to multiple X-ray diagnostic apparatuses. In such a case, the medical-information processing apparatus calculates and notifies the time when the rotating speed of the anode is started to increase with regard to each X-ray diagnostic apparatus. Furthermore, the medical-information processing apparatus acquires, from each X-ray diagnostic apparatus, the state information at the time when the rotating speed of the anode starts to increase and the evaluation of the time when the rotating speed of the anode is started to increase, and it learns the weighting coefficient with regard to each piece of state information.

Specifically, the medical-information processing apparatus, connected to multiple X-ray diagnostic apparatuses, acquires the state information at the time when the rotating speed of the anode is started to increase and the evaluation of the time when the rotating speed of the anode is started to increase each time the rotating speed of the anode increases from the low rotating speed to the high rotating speed with regard to each X-ray diagnostic apparatus. In other words, the medical-information processing apparatus, connected to multiple X-ray diagnostic apparatuses, acquires the combination of the state information and the evaluation during each examination. Then, the medical-information processing apparatus updates the weighting coefficient with regard to each piece of state information on the basis of the acquired combination. Specifically, the medical-information processing apparatus learns the weighting coefficient with regard to each piece of state information during each examination that uses any of the connected X-ray diagnostic apparatuses. Thus, the medical-information processing apparatus, connected to multiple X-ray diagnostic apparatuses, may correctly calculate the time when the rotating speed of the anode is started to increase by using the weighting coefficient that is learned by using lots of data as compared to the case where it is connected to only the X-ray diagnostic apparatus 1.

Furthermore, there may be a case where the medical-information processing apparatus learns the weighting coefficient for each piece of state information with regard to each user. Furthermore, there may be a case where, if the medical-information processing apparatus is connected to multiple X-ray diagnostic apparatuses, which are provided in multiple sites (e.g., multiple hospitals), it learns the weighting coefficient for each piece of state information with regard to each site.

The above-described embodiments may be used in combination as appropriate.

The above-described processor is for example a central processing unit (CPU), a graphics processing unit (GPU), an application specific integrated circuit (ASIC), a programmable logic device (PLD), or a field programmable gate array (FPGA). Furthermore, the programmable logic device (PLD) is for example a simple programmable logic device (SPLD) or a complex programmable logic device (CPLD).

According to the above-described embodiment, the high-voltage generation circuitry 11, the collimator adjustment circuitry 12, the anode drive circuitry 16, the drive circuitry 19, the generation circuitry 23, and the processing circuitry 26 read and execute programs, stored in the memory circuitry 25, to implement their functions; however, this is not a limitation. Instead of storing the programs in the memory circuitry 25, the program may be directly installed in each of the circuitry. In this case, the circuitry reads and executes the directly installed programs to implement the functions.

Each of the circuitry, illustrated in FIG. 1, may be separated or combined as appropriate. For example, the processing circuitry 26 may be separated into image-acquiring control circuitry and control circuitry that implement each function, i.e., the monitoring function 261, the derivation function 262, the rotating-speed control function 263, the image-acquiring control function 264, and the control function 265. Furthermore, for example, the high-voltage generation circuitry 11, the collimator adjustment circuitry 12, the anode drive circuitry 16, the drive circuitry 19, the generation circuitry 23, and the processing circuitry 26 may be arbitrarily combined.

According to at least one of the above-described embodiments, it is possible to provide the X-ray diagnostic apparatus that may promptly start to acquire acquisition images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray tube including a rotary anode; and
processing circuitry configured to:
derive an acquiring condition from a fluoroscopic image, and
start to increase, in accordance with the acquiring condition derived, a rotating speed of the rotary anode from a low rotating speed to a high rotating speed before the X-ray tube finishes emitting an X-ray to acquire the fluoroscopic image.

2. The X-ray diagnostic apparatus according to claim 1, wherein the processing circuitry is configured to start image acquiring in an interval from when the rotating speed of the rotary anode reaches the high rotating speed to when an elapsed time required to increase the low rotating speed to the high rotating speed elapses after the X-ray tube finishes emitting an X-ray to acquire the fluoroscopic image.

3. The X-ray diagnostic apparatus according to claim 1, wherein the processing circuitry is configured to start to increase the rotating speed of the rotary anode from the low rotating speed to the high rotating speed if a variation in a statistic in brightness of pixels of the fluoroscopic image satisfies a determination condition.

4. The X-ray diagnostic apparatus according to claim 3, wherein the determination condition is a condition that the statistic falls within a predetermined range during more than a predetermined time.

5. The X-ray diagnostic apparatus according to claim 1, wherein the processing circuitry is configured to start to increase the rotating speed of the rotary anode from the low rotating speed to the high rotating speed if an operating mechanism is stopped and if a variation in a statistic in brightness of pixels of the fluoroscopic image satisfies a determination condition.

6. The X-ray diagnostic apparatus according to claim 5, wherein the operating mechanism is a couch on which a subject is placed.

7. The X-ray diagnostic apparatus according to claim 5, wherein the operating mechanism is a collimator that adjusts an irradiation range of an X-ray.

8. The X-ray diagnostic apparatus according to claim 1, wherein the processing circuitry is configured to start to increase the rotating speed of the rotary anode from the low rotating speed to the high rotating speed if information indicating that a subject has stopped breathing or information indicating that the subject has received a command to stop breathing is received and if a variation in a statistic in brightness of pixels of the fluoroscopic image satisfies a determination condition.

9. The X-ray diagnostic apparatus according to claim 1, wherein the processing circuitry is configured to start to increase the rotating speed of the rotary anode from the low rotating speed to the high rotating speed if information indicating that a subject has stopped moving or information indicating that the subject has received a command to stop moving is received and if a variation in a statistic in brightness of pixels of the fluoroscopic image satisfies a determination condition.

10. The X-ray diagnostic apparatus according to claim 1, wherein the processing circuitry is configured to start to increase the rotating speed of the rotary anode from the low rotating speed to the high rotating speed if a user has performed a predetermined operation and if a variation in a statistic in brightness of pixels of the fluoroscopic image satisfies a determination condition.

11. The X-ray diagnostic apparatus according to claim 1, wherein the processing circuitry is configured to start to increase the rotating speed of the rotary anode from the low rotating speed to the high rotating speed if a predetermined time has elapsed after the X-ray tube has started to emit an X-ray to acquire the fluoroscopic image and if a variation in a statistic in brightness of pixels of the fluoroscopic image satisfies a determination condition.

12. The X-ray diagnostic apparatus according to claim 1, wherein the processing circuitry is configured to start to increase the rotating speed of the rotary anode from the low rotating speed to the high rotating speed if a user satisfies a position condition and if a variation in a statistic in brightness of pixels of the fluoroscopic image satisfies a determination condition.

13. The X-ray diagnostic apparatus according to claim 1, wherein the processing circuitry is configured to:
perform a process to determine a time when the rotating speed is started to increase from the low rotating speed to the high rotating speed by using at least one of following pieces of information as state information: information that indicates a variation in a statistic in brightness of pixels of the fluoroscopic image, information that indicates whether an operating mechanism is stopped, information that indicates whether a subject has stopped breathing, information that indicates whether the subject has received a command to stop breathing, information that indicates whether the subject has stopped moving, information that indicates whether the subject has received a command to stop moving, information that indicates whether a user has performed a predetermined operation, information that indicates a time that has elapsed after the X-ray tube has started to emit an X-ray to acquire the fluoroscopic image, and information that indicates a position of a user, the processing circuitry performing the process, in accordance with a relationship between the state information at a time when the rotating speed is started to increase from the low rotating speed to the high rotating speed and an evaluation of a time when the rotating speed of the rotary anode is started to increase from the low rotating speed to the high rotating speed, to learn a weighting coefficient with regard to each piece of the state information and determine the time when the rotating speed is started to increase from the low rotating speed to the high rotating speed based on the state information input and the weighting coefficient, and
start to increase the rotating speed of the rotary anode from the low rotating speed to the high rotating speed at the time determined.

14. The X-ray diagnostic apparatus according to claim 1, wherein the processing circuitry is configured to:
derive an irradiation possible condition that may be implemented by using the rotating speed of the rotary anode, and
acquire an acquisition image under the irradiation possible condition if the acquiring condition does not fall within the irradiation possible condition.

15. The X-ray diagnostic apparatus according to claim 1, wherein the processing circuitry is configured to decrease the rotating speed of the rotary anode if the rotating speed of the rotary anode is a rotating speed at which the rotary anode resonates.

16. An X-ray diagnostic apparatus comprising:
an X-ray tube including a rotary anode; and
processing circuitry configured to:
derive an acquiring condition from a fluoroscopic image and derive an irradiation possible condition that may be implemented by using a rotating speed of the rotary anode, and
acquire an acquisition image under the irradiation possible condition if the acquiring condition does not fall within the irradiation possible condition.

17. The X-ray diagnostic apparatus according to claim 16, wherein the processing circuitry is configured to decrease the rotating speed of the rotary anode if the rotating speed of the rotary anode is a rotating speed at which the rotary anode resonates.

18. A medical-information processing apparatus comprising: processing circuitry configured to:
acquire an acquiring condition based on a fluoroscopic image, and
calculate, in accordance with the acquiring condition acquired, a time when a rotating speed of a rotary anode is started to increase from a low rotating speed to a high rotating speed before an X-ray tube, including the rotary anode, finishes emitting an X-ray to acquire the fluoroscopic image.

* * * * *